United States Patent [19]
Oppici et al.

[11] 3,983,109
[45] Sept. 28, 1976

[54] PROCESS FOR RECOVERING CEPHALOSPORIN C FROM A FERMENTATION BROTH AS THE N-(p-NITROBENZOYL) DERIVATIVE

[75] Inventors: Ernesto Oppici; Anacleto Gianantonio, both of Milan, Italy

[73] Assignee: Gruppo Lepetit S.p.A., Milan, Italy

[22] Filed: Dec. 30, 1974

[21] Appl. No.: 537,487

[30] Foreign Application Priority Data
Jan. 3, 1974 United Kingdom.................. 207/74

[52] U.S. Cl. ........................... 260/243 C; 424/246
[51] Int. Cl.² ..................................... C07D 501/12
[58] Field of Search ............................... 260/243 C

[56] References Cited
UNITED STATES PATENTS
3,853,863  12/1974  Jackson et al. ................. 260/243 C

*Primary Examiner*—Nicholas S. Rizzo
*Assistant Examiner*—Jose Tovar
*Attorney, Agent, or Firm*—Theodore Post; C. Kenneth Bjork

[57] ABSTRACT

Cephalosporin C is recovered from its fermentation broth by in situ formation of N-(p-nitrobenzoyl)cephalosporin C which is extracted therefrom and converted to 7-amino-cephalosporanic acid.

6 Claims, No Drawings

PROCESS FOR RECOVERING CEPHALOSPORIN C FROM A FERMENTATION BROTH AS THE N-(p-NITROBENZOYL) DERIVATIVE

BACKGROUND OF THE INVENTION

Processes for the recovery of cephalosporin C by means of reaction of the side chain amino group with acyl halides, alkyl isocyanates, aryl isocyanates and chlorocarbonates to give the corresponding derivatives are already known. See, for example, Belgian Pat. Nos. 758,800 and 807,171; U.S. Pat. No. 3,573,295 3,573,296; and German D.O.S. No. 2,157,693. These processes, however, present some disadvantages such as the use of noxious chemicals which are not easily handled in a large amount, troublesome procedures for the isolation and purification of the reaction products and only moderate recovery yields.

SUMMARY OF THE INVENTION

The process of this invention involves formation of derivatives of cephalosporin C, such as the N-(p-nitrobenzoyl) derivative of cephalosporin C and a salt thereof with an alkali metal or an organic base such as, for example, a tertiary amine. N-(p-nitrobenzoyl) cephalosporin C is a compound which, together with its salts, may be readily converted to 7-aminocephalosporanic acid using conventional techniques.

The conversion of cephalosporin C to N-(p-nitrobenzoyl)cephalosporin C is carried out in an economical way by using p-nitrobenzoyl chloride, a comparatively inexpensive reactant, as the N-(p-nitrobenzoylating) agent. Moreover, only a very simple isolation and purification of the said derivative is needed, since the p-nitrobenzoate of cephalosporin C gives a salt with an alkali metal or with an organic base such as a tertiary amine which separates and crystallizes from organic solvent solutions with a surprising degree of purity, as compared with the usual purities of natural substances recovered from their reaction media. Suitable salts are, for instance, those obtained as the sodium or the N,N-dimethylbenzylamine salt which are readily crystallizable from 1 to 4 carbon alkanols, (1 to 4 carbon)lower alkyl acetates and (1 to 4 carbon)lower aliphatic ketones. Other amines which may be advantageously employed to form a suitable salt are, for instance, N,N-dibenzylamine, N,N-dimethylaniline, N,N-diethylaniline, N,N-diethylcyclohexylamine, N,N-diethylbenzylamine, N-ethylpiperidine and N-methylpyrrolidine.

Another favorable characteristic of the inventive process is the high recovery yield of cephalosporin C p-nitrobenzoate or one of its salts, e.g., its sodium or N,N-dimethylbenzylamine salt, which can range from about 80 to about 95 percent.

The recovery procedure of this invention is not substantially affected by the concentration level of the cephalosporin C in the fermentation broth. It can be carried out on a fermentation broth having a high concentration level of antibiotic substance as well as on a low concentration fermentation broth containing, for instance, 500–600 γ/ml. of antibiotic.

In a preferred mode of carrying out the recovery procedure, a fermentation broth containing cephalosporin C, after filtration with a filter aid, is diluted with about 5 to 15 percent by volume of a water-miscible or partially water-miscible organic solvent such as acetone or ethyl acetate and is cooled to 5° to 10°C. The pH of the fermentation broth is then adjusted to between about 6.5 and about 8 preferably between 7.0 and 7.7 by addition of a base such as aqueous dilute sodium hydroxide, sodium carbonate or sodium bicarbonate. p-Nitrobenzoyl chloride dissolved in a water-miscible or partially water-miscible organic solvent, such as, for instance, acetone or ethyl acetate, is then added slowly with stirring. The value of the pH is constantly maintained between about 6.5 and about 8, preferably between 7.0 and 7.7, by addition of a hydrogen chloride acceptor and the temperature is held in the range of 5° to 10°C. during said addition. The p-nitrobenzoyl chloride is generally employed in a ratio varying from about 1.5 to about 10 molecular proportions per molecular proportion of cephalosporin C. Thereafter, a further addition of acid is made to bring the pH value to 4.5 to 5 and the broth is extracted with a water-immiscible organic solvent such as, for instance, methyl isobutyl ketone, ethyl acetate, propyl acetate or butyl acetate to eliminate impurities. The aqueous phase is acidified with an aqueous dilute mineral acid to pH 2 and then thoroughly extracted with an organic solvent such as methyl isobutyl ketone, butanol, ethyl acetate or the like. The organic phase which may be filtered with charcoal is then dried and evaporated to a smaller volume and the concentrated solution is then treated with an agent capable of providing an alkali metal or amine cation, e.g., sodium 2-ethylhexanoate or a tertiary amine such as N,N-dimethyl benzylamine are advantageously employed. The solid which precipitates on cooling is the sodium or the N,N-dimethylbenzylamine or other salt of the p-nitrobenzoate of cephalosporin C. Although in many instances it is not strictly necessary, since the product thereby obtained already has a satisfactory degree of purity, a simple crystallization from an organic solvent such as, for instance, a 1 to 4 carbon alkanol or a mixture of such lower alkanols afford a high purity product which allows direct conversion to 7-aminocephalosporanic acid in high yields. Alternatively, the concentrated organic solution is chilled and the free acid is precipitated by addition of a (1 to 4 carbon)lower alkyl ether.

For conversion to 7-aminocephalosporanic acid, the usual and known procedures are suitably employed. For instance, high conversion yields are achieved by operating substantially according to the method described in U.S. Pat. No. 3,575,970, as illustrated in following Example 6.

The following additional description and examples further describe the invention and the manner and process of making and using it to enable the art skilled to make and use the same and set forth the best mode contemplated by the inventors of carrying out the invention.

EXAMPLE 1

Twenty five liters of filtered fermentation broth containing 62 g. of cephalosporin C is diluted with 15 percent (volume) of acetone and cooled to 5° to 10°C. The pH of the mixture is then adjusted to 7.5 by adding aqueous 10 percent sodium hydroxide, and 55 g. of p-nitrobenzoyl chloride dissolved in 100 ml. of acetone is added slowly with stirring. During the addition of the latter, the pH value is maintained between 7.5 and 8 by addition of aqueous dilute sodium hydroxide or sodium carbonate. When the addition is completed, the mixture is allowed to stand at 10°C. until the pH value of the mixture becomes steady. Dilute sulfuric acid is then added to a pH of 6.5 and the acetone is distilled off at room temperature under vacuum. The pH is then brought to 4.5 by further addition of dilute sulfuric acid and the mixture is extracted three times with ¼ volume of methyl isobutyl ketone. The organic extracts are discarded and the aqueous phase is acidified to a pH of 2 with dilute sulfuric acid, then extracted 4 times with a 1/6 volume of ethyl acetate. The combined organic extracts are washed with an aqueous saturated solution of NaCl and, after drying over $Na_2SO_4$, filtered with charcoal and concentrated to a volume of about 1 liter. To the resulting solution, sodium ethylhexanoate is added to a pH of 6. The solid precipitate which forms on cooling is recovered by filtration and washed on the filter with light petroleum. The product, which is the sodium salt of N-(p-nitrobenzoyl)cephalosporin C, already shows a satisfactory degree of purity. It may be further crystallized from methanol: isopropanol 1:3 to give 85.5 g. of a product having a 4.56 percent loss on drying (90 percent yield calculated on the anhydrous material). The product after drying shows the following physical characteristics:

$[\alpha]_D^{20} = +99.6$ [ C=1% (w/v) in water ]
$\lambda$ max = 264 m$\mu$
$E_{1\ cm}^{1\%} = 306.5$ in water

EXAMPLE 2

The concentrated ethyl acetate solution of N-(p-nitrobenzoyl)cephalosporin C obtained pursuant to the procedure of Example 1 is diluted with isopropyl ether. The precipitate which forms on cooling is then recovered by filtration and crystallized twice from a mixture of isopropanol and light petroleum, giving 67.2 g. (80 percent) of the N-(p-nitrobenzoate) of cephalosporin C having the following physical characteristics:

$[\alpha]_D^{20} = +78.3$ [ C=1% (w/v) in methanol]
$\lambda$ max = 264 m$\mu$
$E_{1\ cm}^{1\%} = 348$ in methanol Analysis: calc. for $C_{23}H_{24}N_4O_{11}S$: C 48.9; H 4.2; N 9.9; S 5.6. found C 48.15; H 4.25; N 9.6; S 5.36.

Instead of crystallizing the crude precipitate to obtain the free acid, it may be transformed to the corresponding sodium salt by solution in acetone followed by addition of sodium ethylhexanoate. The yield is 85 percent.

EXAMPLE 3

To 50.4 liters of the filtered fermentation broth containing 93.8 g. (0.226 mole) of cephalosporin C is added 2.5 liters of ethyl acetate and the pH is adjusted to 7.5 by adding aqueous 10 percent sodium carbonate. To this mixture, 294 g. (1.58 moles) of p-nitrobenzoyl chloride dissolved in five liters of ethyl acetate is added. During the addition, the value of the pH is constantly maintained between 7 and 7.7 by addition of aqueous sodium carbonate and the temperature is maintained between 5° and 10°C. After stirring for 30 minutes, the mixture is brought to a pH of 5 by addition of 30 percent $H_2SO_4$ then extracted with ethyl acetate. The organic phase is discarded and the aqueous phase is acidified to pH 2 and extracted five times with four liters of ethyl acetate. The resulting organic extract is dried over $MgSO_4$ and concentrated under vacuum at room temperature to a small volume. On adding about 3 volumes of isopropyl ether, a solid precipitates which, after standing for 2 hours at 0°C., is filtered, yielding 140 g. of crude N-(p-nitrobenzoyl) cephalosporin C (75 percent purity). The yield of the recovery is 87 percent calculated on the pure material. This product is readily transformed into 7-aminocephalosporanic acid without any further purification.

EXAMPLE 4

Twenty liters of filtered fermentation broth containing 72 g. of cephalosporin C is reacted with p-nitrobenzoyl chloride and extracted as described in Example 3. The organic extract is then dried over $MgSO_4$ and concentrated under vacuum to a small volume. 43.2 Grams of N,N-dimethylbenzylamine is then added to the solution, giving a solid precipitate. The mixture is further concentrated and allowed to stand for 2 hours at 0°C. The resulting solid precipitate is recovered by filtration, yielding 139 g. of the salt of N-(p-nitrobenzoyl)cephalosporin C with one molecule of N,N-dimethylbenzylamine. This salt has an 80 percent purity and may be transformed directly into 7-aminocephalosporanic acid in high yields. The yield of the recovery is 92 percent calculated on the pure material. The N,N-dimethylbenzylamine salt of N-(p-nitrobenzoyl)cephalosporin C has the following physical characteristics:

$[\alpha]_D^{20} = +63.6$ [ C=1% (w/v) in methanol ]
$\lambda$ max = 263 m$\mu$
$E_{1\ cm}^{1\%} = 283$ in methanol

EXAMPLE 5

Twenty five liters of fermentation broth containing 22.5 g. of cephalosporin C (900 $\mu$g/ml) is reacted with 70 g. of p-nitrobenzoyl chloride and the reaction product is extracted from the aqueous medium pursuant to the procedure of Example 3. Yield 34.4 g. of crude N-(p-nitrobenzoyl)cephalosporin C (80 percent purity). The yield of the recovery is 90 percent calculated on the pure material.

EXAMPLE 6

Fifty grams (80 percent purity) of the N,N-dimethylbenzylamine salt of N-(p-nitrobenzoyl)cephalosporin C obtained pursuant to the procedure of Example 4 is suspended in 500 ml. of anhydrous dichloromethane and 10 ml. of triethylamine and 9 ml. of N,N-dimethylaniline are added thereto. To this mixture, 48 ml. of trimethylchlorosilane is added at room temperature. After 1 hour, a further addition of 48 ml. of N,N-dimethylaniline is made and the solution is cooled to −60°C. Then 37.5 g. of $PCl_5$ is added and the temperature is maintained at −40°C. for 2 hours. When the reaction is completed, the mixture is cooled to −70°C. and 360 ml. of anhydrous butanol containing 12 ml. of N,N-dimethylaniline is added thereto, keeping the temperature at −40°C. for a further 2 hours. The reaction mixture is finally poured into a solution of 320 ml. of water and 180 ml. of methanol and the pH is adjusted to 3.5 by adding ammonium hydroxide. After standing overnight at 5°C., the resulting solid precipitate is recovered by filtration. The product after washing with methanol and acetone is dried, giving 14.5 g. of 7-aminocephalosporanic acid showing a spectrophotometric purity degree of 99 percent.

EXAMPLE 7

Twenty grams (75 percent purity) of N-(p-nitrobenzoyl)cephalosporin C obtained pursuant to the procedure of Example 3 is suspended in 240 ml. of anhydrous dichloromethane. After addition of 5 ml. of triethylamine and 9 ml. of N,N-dimethylaniline, 22.4 ml. of trimethylchlorosilane is added at room temperature. After 1 hour, 22.4 ml. of N,N-dimethylaniline is added and the solution is cooled to −60°C. Then 18.6 g. of PCl$_5$ is added at −40°C. When the reaction is completed, the mixture is cooled to −70°C. and 180 ml. of butanol containing 4 ml. of N,N-dimethylaniline is added. The reaction mixture is maintained for a further 2 hours at −40°C., then it is poured into a solution of 210 ml. of water and 110 ml. of methanol and the pH is adjusted to 3.5 by addition of ammonium hydroxide. The resulting precipitated product is washed with methanol and acetone and dried, to yield 6.9 g. of 7-aminocephalosporanic acid showing a 97 percent purity degree (spectrophotometrically determined).

What is claimed is:

1. A process for the high recovery yield of cephalosporin C from a fermentation broth thereof characterized in that cephalosporin C is
   a. transformed into its N-(p-nitrobenzoyl) derivative by mixing its fermentation broth diluted with ca. 5 to 15 percent by volume of a water-miscible or partially water-miscible organic solvent with about 1.5 to about 10 molecular proportions of p-nitrobenzoyl chloride per molecular proportion of cephalosporin C in the presence of a hydrochloric acid acceptor and at a pH of about 6.5 to about 8 and a temperature of about 5° to 10°C, then adjusting the pH to 4.5 to 5,
   b. extracting said derivative from the reaction mixture with a water-immiscible organic solvent to eliminate impurities and recovering it as a high purity crystalline product by concentration and filtration of the resultant precipitates or by precipitation as a salt of an alkali metal or of an organic amine and filtration of said precipitate.

2. The process of claim 1 wherein the reaction with p-nitrobenzoyl chloride is carried out at a pH of from about 6.5 to about 8 at a temperature between about 5° and about 10°C.

3. The process of claim 1 wherein the extraction is carried out at a pH of 2 with a water-immiscible organic solvent selected from the group consisting of methyl isobutyl ketone, ethyl acetate and butanol.

4. The process of claim 1 wherein the recovery from the organic extract is carried out by adding an agent providing an alkali metal cation or a tertiary amine to form the corresponding salt as a precipitate.

5. The process of claim 1 wherein the N-(p-nitrobenzoyl)cephalosporin C is precipitated from the organic extract by addition of an agent selected from the group of sodium 2-ethylhexanoate and N,N-dimethylbenzylamine.

6. The process of claim 1 wherein the N-(p-nitrobenzoyl)cephalosporin C is recovered from the organic extract as a precipitate by concentration to small volume and addition of a lower alkyl ether.

* * * * *